United States Patent
Lengyel et al.

(10) Patent No.: US 9,127,293 B2
(45) Date of Patent: Sep. 8, 2015

(54) RECEPTOR-MEDIATED DELIVERY: COMPOSITIONS AND METHODS

(75) Inventors: Ernst Lengyel, Chicago, IL (US); Anthony Kossiakoff, Chicago, IL (US); Joseph Piccirilli, Chicago, IL (US)

(73) Assignee: The University of Chicago, Chicago, IL (US)

( * ) Notice: Subject to any disclaimer, the term of this patent is extended or adjusted under 35 U.S.C. 154(b) by 630 days.

(21) Appl. No.: 12/375,179

(22) PCT Filed: Jul. 26, 2007

(86) PCT No.: PCT/US2007/074493
§ 371 (c)(1), (2), (4) Date: Jan. 26, 2009

(87) PCT Pub. No.: WO2008/014404
PCT Pub. Date: Jan. 31, 2008

(65) Prior Publication Data
US 2009/0317855 A1    Dec. 24, 2009

Related U.S. Application Data

(60) Provisional application No. 60/833,850, filed on Jul. 26, 2006.

(51) Int. Cl.
*A61B 5/055* (2006.01)
*C12N 15/87* (2006.01)
*A61K 48/00* (2006.01)

(52) U.S. Cl.
CPC .............. *C12N 15/87* (2013.01); *A61B 5/055* (2013.01); *A61K 48/00* (2013.01)

(58) Field of Classification Search
CPC .............. C07K 14/57554; G01N 2333/5756; G01N 24/00; C12N 2501/315; A61K 38/2257; A61K 49/06; A61K 49/14; A61K 49/085; A61K 49/08; A61B 5/055; G01R 33/20
USPC .......................... 514/11.5; 530/399
See application file for complete search history.

(56) References Cited

U.S. PATENT DOCUMENTS

| | | | |
|---|---|---|---|
| 5,057,301 A | 10/1991 | Wilbur et al. | |
| 6,492,498 B1 | 12/2002 | Vallera et al. | |
| 6,605,426 B1 | 8/2003 | Goldmakher et al. | |
| 6,673,333 B1 | 1/2004 | Meade | |
| 7,306,785 B2 | 12/2007 | Brogan | |
| 2003/0004236 A1* | 1/2003 | Meade | 524/98 |
| 2003/0049203 A1 | 3/2003 | Elmaleh | |
| 2003/0105000 A1* | 6/2003 | Pero et al. | 514/12 |
| 2004/0204377 A1 | 10/2004 | Rana | |
| 2005/0008617 A1 | 1/2005 | Chen et al. | |
| 2005/0202077 A1 | 9/2005 | Watson et al. | |
| 2006/0040882 A1 | 2/2006 | Chen et al. | |
| 2009/0104123 A1* | 4/2009 | Yang et al. | 424/9.3 |
| 2009/0317335 A1 | 12/2009 | Lin et al. | |

FOREIGN PATENT DOCUMENTS

| | | | |
|---|---|---|---|
| WO | WO 02/087632 | 11/2002 | |
| WO | WO 2006/080022 A2 * | 8/2006 | ............ A61K 49/10 |
| WO | WO 2007/030571 | 3/2007 | |
| WO | WO 2007/030802 | 3/2007 | |

OTHER PUBLICATIONS

Turkington, R.W. (Cancer Res. 1974 34:758-763).*
Yanai et al. (J. Endocrinological Invest. 1980 3:63-66).*
Li et al. (Oncogene, Nov. 7, 2005, 25:1896-1902).*
Asai-Sato et al. (Int. J. Cancer, Feb. 7, 2005, 115:539-544).*
Knopp et al. (Mol. Cancer Therapeutics, Apr. 2003, 2: 419-426).*
Ibragimova and Eade (Biophysical Journal, Oct. 1999, vol. 77, pp. 2191-2198).*
Skolnick et al. (TIBTECH 18:34-39, 2000).*
Burgess et al. (J of Cell Bio. 111:2129-2138, 1990).*
Rudikoff et al. (PNAS USA, 1982, 79: 1979-1983).*
Peterson et al. (Protein. Engineering, Design, & Selection, 2004, 17(5): 417-424).*
Amarzguioui, M. et al., "Tolerance for mutations and chemical modifications in a siRNA," Nucl. Acids. Res. (2003) 31:589-595.
Asai-Sato, M. et al., "Prolactin inhibits apoptosis of ovarian carcinoma cells induced by serium starvation or cisplatin treatment," Int. J. Cancer (2005) 115:539-544.
Auersperg, N. et al., "Ovarian surface epithelium: biology, endocrinology, and pathology," Endocr. Rev. (2001) 22:255-288.
Bader, T. et al., "Nuclear accumulation of interferon γ," Proc. Natl. Acad. Sci. USA (1994) 91:11831-11835.
Bijsterbosch, M.K. et al., "Modulation of plasma protein binding and in vivo liver cell uptake of phosphorothioate oligodeoxynucleotides by cholesterol conjugation," Nucl. Acids Res. (2000) 28:2717-2725.
Birchmeier, C. et al., "Met, metastasis, motility and more," Nat. Rev. Mol Cell Biol. (2003) 4:915-925.
Buckley, A.R. et al., "Rapid activation of protein kinase C in isolated rat liver nuclei by prolactin, a known hepatic mitogen," Proc. Natl. Acad. Sci. USA (1988) 85:8649-8653.
Clevenger, C.V. et al., "Interleukin-2 driven nuclear translocation of prolactin in cloned T-lymphocytes," Endocrinology (1990) 127:3151-3159.

(Continued)

*Primary Examiner* — Peter J Reddig
(74) *Attorney, Agent, or Firm* — Valauskas Corder LLC

(57) ABSTRACT

Compositions and methods for delivering an agent to a cell comprising a prolactin receptor are provided. Also provided is a method of inhibiting a breast, ovarian or prostate cancer cell, where the method includes a step of contacting the cell with a complex comprising a prolactin receptor ligand linked to at least one of an RNAi-inducing agent, a polynucleotide sequence encoding a polypeptide, an miRNA, a cytotoxic moiety, a chemotherapeutic moiety, a radioactive moiety or a nanoparticle. Methods of detecting a cancer cell expressing a prolactin receptor are also provided.

6 Claims, 13 Drawing Sheets

(56) References Cited

OTHER PUBLICATIONS

Clevenger, C.V. et al., "Requirement of nuclear prolactin for interleukin-2-stimulated proliferation of T lymphocytes," Science (1991) 253:77-79.

Clevenger, C.V., "Regulation of interleukin 2-driven T-lymphocyte proliferation by prolactin," Proc. Natl. Acad. Sci. USA (1990) 87:6460-6464.

Clevenger, C.V., "Role of prolactin/prolactin receptor signaling in human breast cancer," Breast. Dis. (2003) 18:75-86.

Corps, A.N. et al., "Hepatocyte growth factor stimulates motility, chemotaxis and mitogenesis in ovarian carcinoma cells expressing high levels of c-met," Int. J. Cancer (1997) 73:151-155.

Cutler, C.S. et al., "Utilization of metabolic, transport and receptor-mediated processes to deliver agents for cancer diagnosis," Adv. Drug Del. Rev. (1999) 37(1-3):189-211.

Czauderna, F. et al., "Structural variations and stabilising modifications of synthetic siRNAs in mammalian cells," Nucl. Acids Res. (2003) 31:2705-2716.

Elbashir, S.M. et al., "Functional anatomy of siRNAs for mediating efficient RNAi in *Drosophila melanogaster* embryo lysate," EMBO J. (2001) 20:6877-6888.

Fire, A. et al., "Potent and specific genetic interference by double-stranded RNA in *Caenorhabditis elegans*," Nature (1998) 391:806-811.

Gill, S. et al., "Expression of prolactin receptors in normal, benign, and malignant breast tissue: an immunohistological study," J. Clin. Pathol. (2001) 54:956-960.

Glasow, A. et al., "Mutational analysis of the PRL receptor gene in human breast tumors with differential PRL receptor protein expression," J. Clin. Endo. Metab. (2001) 86(8):3826-3832.

Gonnella, P.A. et al., "Prolactin is transported across the epithelium of the jejunum and ileum of the suckling rat," J. Cell Physiol. (1989) 140(1):138-149.

Hammond, S.M. et al., "An RNA-directed nuclease mediates post-transcriptional gene silencing in *Drosophila* cells," Nature (2000) 404:293-296.

Hannon, G.J., "RNA interference," Nature (2002) 418:244-251.

Harborth, J. et al., "Identification of essential genes in cultured mammalian cells using small interfering RNAs," J. Cell Sci. (2001) 114:4557-4565.

Hartmann, G. et al., "The motility signal of scatter factor/hepatocyte growth factor mediated through the receptor tyrosine kinase met requires intracellular action of Ras," J. Biol Chem. (1994) 269:21936-21939.

Jans, D.A. et al., "The cytokine interleukin-5 (IL-5) effects cotransport of its receptor subunits to the nucleus in vitro," FEBS Lett. (1997) 410:368-372.

Kligenberg, O. et al., "Inability of the acidic fibroblast growth factor mutant K132E to stimulate DNA synthesis after translocation into cells," J. Biol. Chem. (1998) 273:11164-11172.

Krutzfeldt, J. et al., "Silencing of microRNAs in vivo with 'antagomirs'," Nature (2005) 438:685-689.

Lengyel, E. et al., "C-met overexpression in node-positive breast cancer identifies patients with poor clinical outcome independent of Her2/neu," Int. J. Cancer (2005) 113:678-682.

Liberman, J. et al., "Interfering with disease: opportunities and roadblocks to harnessing RNA interference," Trends Mol. Med. (2003) 9:397-403.

Liby, K. et al., "Prolactin overexpression by MDA-MB-435 human breast cancer cells accelerates tumor growth," Breast Cancer Res. Treat. (2003) 79(2):241-252.

Lobie, P.E. et al., "Receptor-mediated nuclear translocation of growth hormone," J. Biol. Chem. (1994) 269:21330-21339.

Lorenz, C. et al., "Steroid and lipid conjugates of siRNAs to enhance cellular uptake and gene silencing in liver cells," Bioorg. Med. Chem. Lett. (2004) 14:4975-4977.

Maggiora, P. et al., "The RON and MET oncogenes are co-expressed in human ovarian carcinomas and cooperate in activating invasiveness," Exp. Cell Res. (2003) 288:382-389.

Manoharan, M., "RNA interference and chemically modified small interfering RNAs," Curr. Opin. Chem. Biol. (2004) 8:570-579.

Masckauchuan, N.T.H. et al., "A new photoactivatable reagent capable of transferring a radiolabel to target proteins. Application to the human growth hormone—rat liver prolactin receptor interaction," Bioconj. Chem. (1998) 9:507-511.

McCaffrey, A.P. et al., "RNA interference in adult mice," Nature (2002) 418:38-39.

Munoz, R. et al., "Effect of mutation of cytoplasmic receptor domain and of genistein on transport of acidic fibroblast growth factor into cells," Oncogene (1997) 15:525-536.

Paddison, P.J. et al., "Short hairpin RNAs (shRNAs) induce sequence-specific silencing in mammalian cells," Genes Dev. (2002) 16:948-958.

Patel, D.D. et al., "Node negative breast carcinoma: hyperprolactinemia and/or overexpression of p53 as an independent predictor of poor prognosis compared to newer and established prognosticators," Oncol. (1996) 62(2):86-92.

Rakowicz-Szulczynska, E.M. et al., "Chromatin binding of epidermal growth factor, nerve growth factor, and platelet-derived growth factor in cells bearing the appropriate surface receptors," Proc. Natl. Acad. Sci. USA (1986) 83:3728-3732.

Rakowicz-Szulczynska, E.M. et la., "Nerve growth factor receptors in chromatin of melanoma cells, proliferating melanocytes, and colorectal carcinoma cells in vitro," Cancer Res. (1988) 48:7200-7206.

Rao, Y-P. et al., "Nuclear translocation of prolactin: collaboration of tyrosine kinase and protein kinase C activation in rat Nb2 node lymphoma cells," J. Cell Physiol. (1995) 163:266-276.

Reynolds, A. et al., "Rational siRNA design for RNA interference," Nat. Biotechnol. (2004) 22:326-330.

Reynolds, C. et al., "Expression of prolactin and its receptor in human breast carcinoma," Endocrinology (1997) 138(12):5555-5560.

Rojas, et al., "Genetic engineering of proteins with cell membrane permeability," Nature Biotech. (1998) 16:370-375.

Sattler, M. et al., "Therapeutic targeting of the receptor tyrosine kinase Met," Cancer Treat. Res. (2004) 119:121-138.

Schiffelers, R.M. et al., "Cancer siRNA therapy by tumor selective delivery with ligand-targeted sterically stabilized nanoparticle," Nuc. Acids Res. (2004) 32(19):e149, 10 pages.

Shayesteh, L. et al., "PIK3CA is implicated as an oncogene in ovarian cancer," Nat. Genet. (1999) 21:99-102.

Silva, J.M. et al., "RNA interference: a promising approach to antiviral therapy?" Trends Mol. Med. (2002) 8:505-508.

Smith, R.M. et al., "Preparation and characterization of a colloidal gold-insulin complex with binding and biological activities identical to native insulin," J. Histochem. Cytochem. (1988) 36:359-365.

Smith, R.M. et al., "Ultrastructural evidence for the accumulation of insulin in nuclei of intact 3T3-L1 adipocytes by an insulin-receptor mediated process," Proc. Natl. Acad. Sci. USA (1987) 84:459-463.

Soler, A.P. et al., "Immunological demonstration of the accumulation of insulin, but not insulin receptors, in nuclei of insulin-treated cells," Proc. Natl. Acad. Sci. USA (1989) 86:6640-6644.

Song, E. et al., "Antibody mediated in vivo delivery of small interfering RNAs via cell-surface receptors," Nature Biotech. (2005) 23(6):709-717.

Song, E. et al., "RNA interference targeting Fas protecs mice from fulminant hepatitis," Nat. Med. (2003) 9:347-351.

Soutschek, J. et al., "Therapeutic silencing of an endogenous gene by systemic administration of modified siRNAs," Nature (2004) 432:173-178.

Sowter, H.M. et al., "Hepatocyte growth factor (HGF) in ovarian epithelial tumour fluids stimulates the migration of ovarian carcinoma cells," Int. J. Cancer (1999) 83:476-480.

Touraine, P. et al., "Increased expression of prolactin receptor gene assessed by quantitative polymerase chain reaction in human breast tumors versus normal breast tissues," J. Clin. Endo. Metab. (1998) 83:2:667-674.

Usman, N. et al., "Nuclease-resistant synthetic ribozymes: developing a new class of therapeutics," J. Clin. Invest. (2000) 106:1197-1202.

(56) References Cited

OTHER PUBLICATIONS

Webb, C.P. et al., "Evidence for a role of Met-HGF/SF during Ras-mediated tumorigenesis/metastatsis," Oncogene (1998) 17:2019-2025.

Wiedlocha, A. et al., "Dual mode of signal transduction by externally added acidic fibroblast growth factor," Cell (1994) 76:1039-1051.

Wu, W. et al., "S179D prolactin increases vitamin D receptor and p21 through up-regulation of short 1b prolactin receptor in human prostate cancer cells," Cancer Res. (2005) 65(16):7905-7915.

Zamore, P.D., "Ancient pathways programmed by small RNAs," Science (2002) 296:1265-1269.

Zhang, Y. et al., "In vivo knockdown of gene expression in brain cancer with intravenous RNAi in adult rats," J. Gene Med. (2003) 5:1039-1045.

International Search Report and Written Opinion for Application No. PCT/US07/74493 dated Sep. 26, 2008 (11 pages).

U.S. Appl. No. 60/793,454, filed Apr. 20, 2006, Hybrid Nanomaterials as Multimodal Imaging Contrast Agents, Inventorship: Wenbin Lin, William Rieter, Kathryn Taylor, Jason Kim.

* cited by examiner

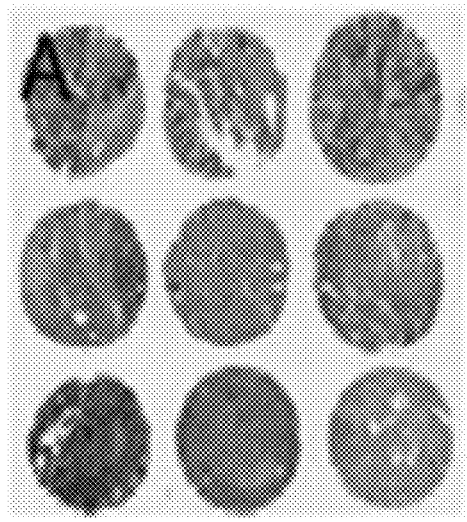
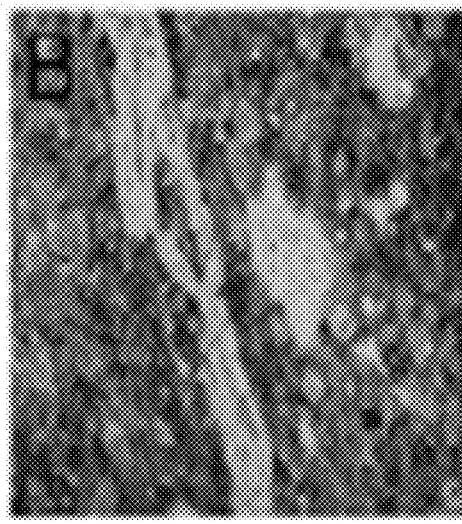
FIG. 1A  FIG. 1B
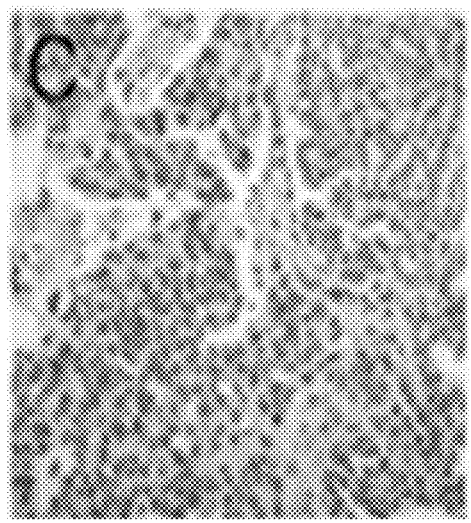
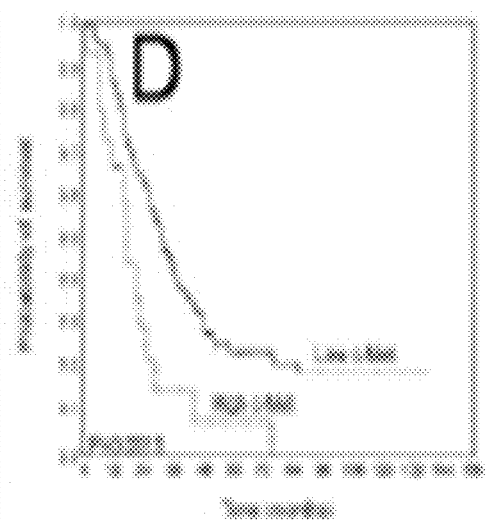
FIG. 1C  FIG. 1D

RECEPTOR-MEDIATED DELIVERY: COMPOSITIONS AND METHODS

CROSS-REFERENCE TO RELATED APPLICATIONS

This application is a national stage filing under 35 U.S.C. 371 of International Application No. PCT/US2007/074493 filed Jul. 26, 2007, which claims priority to U.S. Provisional Application No. 60/833,850 filed Jul. 26, 2006. These applications are incorporated herein by reference in their entireties.

STATEMENT REGARDING FEDERALLY SPONSORED RESEARCH

Not applicable.

INTRODUCTION

A fundamental challenge in developing effective therapeutic agents is achieving efficient, specific delivery of the agents to tissues in vivo. This limitation is universal for all types of agents, including, for example, small molecules, peptides, proteins and DNA/RNA. This obstacle has hampered the translation of research initiatives to their clinical applications. For example, although gene therapy has been contemplated as a treatment for cancer since at least the 1980's, this treatment modality has been plagued by lack of efficient delivery systems, lack of sustained expression and host immune reactions.

An RNA-based gene silencing system termed "RNA interference," or "RNAi," has been investigated. RNAi is a post-transcriptional process wherein a small single- or double-stranded RNA molecule induces sequence-specific degradation of its homologous messenger RNA (mRNA). It has been hypothesized that the underlying mechanism for RNA interference evolved as a natural defense mechanism against foreign viral DNA or RNA. The discovery of RNAi has resulted in a flurry of research activity with the ultimate goal of harnessing this tool for use in functional genomics, drug discovery and medicine.

In vitro, RNAi has proven to have several advantages over other gene silencing techniques, such as antisense technology. For example, RNAi results in more specific inhibition of gene expression, and induces the same level of silencing at much lower concentrations than antisense nucleic acids. However, as with delivery of other agents to cells within the body, obstacles to delivering short RNA fragments to cells in vivo have limited the therapeutic potential of RNAi.

Several formats for in vivo delivery of RNAi reagents currently exist, but these are not generally compatible with clinical use. For example, hydrodynamic tail vein injection in mice has proven effective, but also has resulted in right-sided heart failure, which clearly limits its therapeutic applicability. Other methods that have been investigated include delivery of RNAi reagents with a variety of lipid-based reagents or viral vectors, or delivery via linking RNAi reagents to peptides, carbohydrate moieties or antibodies or antibody fragments. These methods have resulted in varying degrees of uptake by cells and variable silencing efficacy. In addition, Fab antibody fragments directed against specific cell-surface targets and non-covalently attached to protamine have been used to deliver short interfering RNAs (siRNAs) to HIV-infected cells and ErbB2-expressing cancer cells. (Song et al., Nature Biotechnology 23(6): 709-717, (June 2005)). However, while the use of an Fab may provide specificity towards a targeted cell surface receptor, producing the parent antibody from which the Fab is made is technically complex, due in part to the need to first isolate and stabilize the target receptor from the cell membrane prior to employing hybridoma technology.

Toxins have also been considered as potential anti-cancer agents; however, their application for cancer treatment is limited by the ability to deliver the toxin to specific cancer cells and not surrounding cells. Toxins are thought of as having a highly effective potency, but there remains a need for precise and efficient delivery to minimize side effects on healthy cells.

SUMMARY OF THE INVENTION

In one aspect, the invention provides a method for delivering an agent to a cell expressing a prolactin receptor. The method includes contacting the cell with a complex comprising the agent coupled to a prolactin receptor ligand. The agent is suitably an RNAi-inducing agent or a cytotoxic moiety. However, the inventors have discovered that the method is broadly applicable, and accordingly, other therapeutic and/or imaging agents may be delivered by way of the invention.

In another aspect, the invention provides a method of inhibiting expression of an mRNA in a cell expressing a prolactin receptor. The method includes contacting the cell with a complex comprising an RNAi-inducing agent coupled to a prolactin receptor ligand, wherein the RNAi-inducing agent is complementary to at least a portion of the mRNA.

In a further aspect, the invention provides a method of inhibiting a cancer cell expressing or over-expressing a prolactin receptor, comprising contacting the cell with a complex comprising prolactin receptor ligand linked to at least one of a RNAi-inducing agent, a polynucleotide sequence encoding a polypeptide, a micro RNA (miRNA), a cytotoxic moiety, a chemotherapeutic moiety, a radioactive moiety or a nanoparticle.

In yet another aspect, the invention provides a method of detecting a cancer cell comprising a prolactin receptor. The method includes steps of: contacting a tissue suspected of comprising a cancer cell with a complex comprising a prolactin receptor ligand coupled to a marker; detecting levels of the marker present in the tissue; and correlating elevated levels of marker relative to control tissue with the presence of a cancer cell in the tissue.

The invention also provides a complex comprising an agent coupled to a prolactin receptor ligand.

BRIEF DESCRIPTION OF THE DRAWINGS

FIG. 1A shows hemotoxylin and eosin stained microarrays of ovarian cancers stained using a c-Met antibody. FIG. 1B shows positive staining in a serous ovarian cancer tissue section. FIG. 1C shows a negative control. All images are 250× magnification. FIG. 1D is a graph showing correlation of patient survival and c-Met overexpression.

DESCRIPTION OF ILLUSTRATIVE EMBODIMENTS

Figure 2:
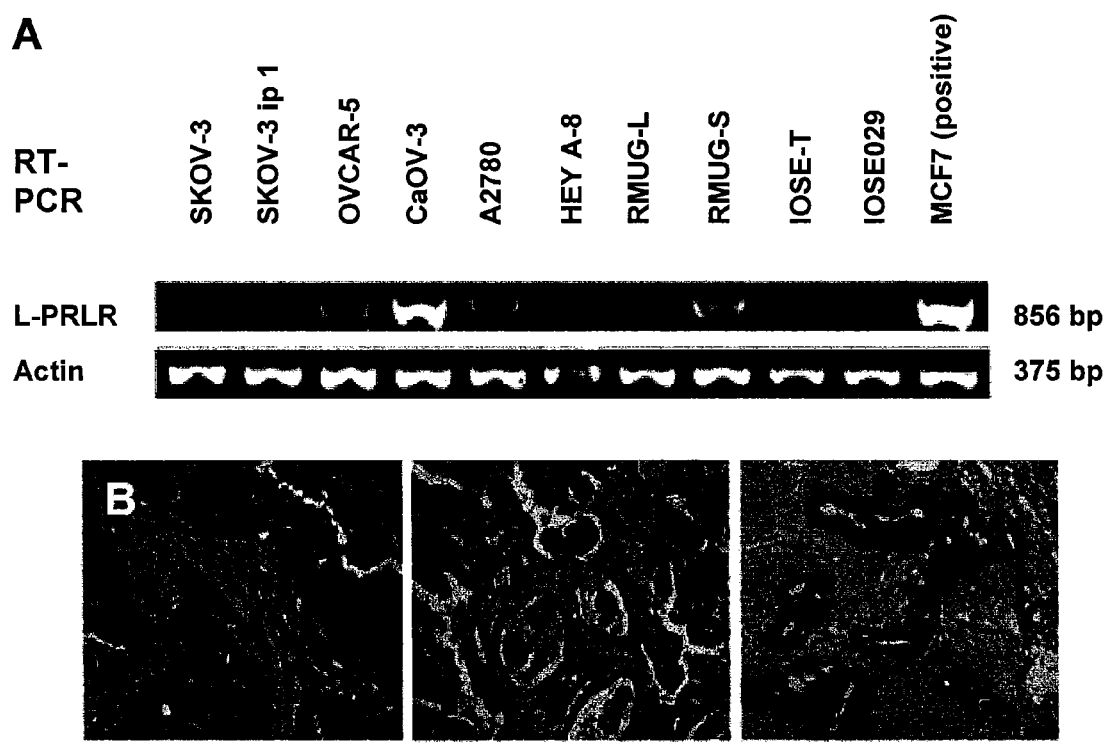
FIG. 2A shows results of RT-PCR analysis demonstrating expression of human prolactin receptor mRNA in ovarian cancer cell lines and a breast tumor cell line.
FIG. 2B shows representative staining of 3 human ovarian cancer tissues using a human prolactin receptor antibody.

The invention provides compositions and methods for specific and efficient in vivo delivery of an agent to a cell by receptor-mediated endocytosis. In general, the invention provides for delivery of an agent to a cell by contacting the cell with a complex of the agent and a prolactin receptor ligand, where the prolactin receptor is expressed on the cell. In particular, ligands specific for the prolactin receptor may be coupled to the agent to be delivered. The compositions and methods will be particularly useful in the treatment of cancers or other diseases in which prolactin receptors are upregulated and/or overexpressed on the cancer cell surface. However, the methods are also broadly applicable to any situation where specific delivery of an agent to a cell is needed.

Prolactin Receptor

The prolactin receptor is involved in the growth and differentiation of various cells. Prolactin receptors have been identified in a number of cells and tissues, including the mammary gland, organs of the reproductive system, central nervous system, pituitary, adrenal cortex, skin, bone, lung, heart, liver, pancreas, GI tract, kidney and lymphoid tissues. Human growth hormone (hGH), human prolactin (hPRL) and human placental lactogen (hPL) all specifically bind the prolactin receptor with high affinity.

In some embodiments, the invention is particularly well-suited to differentially deliver agents to cells that overexpress the prolactin receptor. As used herein, a prolactin receptor is "overexpressed" when it is present on the surface of a cell in an amount that is statistically significantly greater than a suitable control cell. In some embodiments, the prolactin receptor is present on the cell surface at least about 1.5-fold, 2-fold, 5-fold, 10-fold, 100-fold or 1000-fold greater than a suitable control cell. For example, over 80% of breast tumors overexpress the prolactin receptor by as much as 10- to 1000-fold over normal breast tissue. Moreover, about 80% of all ovarian cancer cells in human ovarian cancer samples express the prolactin receptor, while the adjacent, surrounding normal tissue does not express the receptor. Prostate cancer cells also have been shown to overexpress prolactin receptors. Accordingly, the invention is particularly suitable for specific delivery of an agent to ovarian cancer cells, breast cancer cells and prostate cancer cells.

Ligands

A "prolactin receptor ligand," as used herein, refers to an entity that binds the prolactin receptor and induces receptor-mediated endocytosis of the entity, regardless of whether downstream biological effects of prolactin receptor binding are observed. As will be appreciated, no particular level of binding specificity is required, and acceptable levels of specificity will depend on the application. Suitable prolactin receptor ligands include human placental lactogen and variants thereof (including truncated or modified forms), prolactin and variants thereof (including truncated or modified forms) and human growth hormone (hGH) (including truncated or modified forms). Selection of a suitable prolactin receptor ligand will depend on, e.g., the agent to be delivered, the coupling strategy to be used, and the degree of receptor activation desired, if any.

Agents

An "agent," as used herein, refers to any chemical or biological entity that may be internalized into a cell via a prolactin receptor when coupled to a prolactin receptor ligand. The agent may have a positive charge to aid in the ability of the agent to be internalized.

Non-limiting examples of suitable agents for delivery to cells by way of the invention include RNAi-inducing agents, polynucleotide sequences, micro RNA ("miRNA"), antagomirs, cytotoxic moieties, chemotherapeutic moieties, radioactive moieties, imaging moieties and nanoparticles.

An "RNAi-inducing agent," as the term is used herein and in the art, encompasses RNA molecules or vectors whose presence within a cell results in RNA interference and leads to reduced expression of a transcript to which the RNAi-inducing entity is targeted. Suitably, for some embodiments, delivery of an RNAi-inducing agent reduces expression of the target transcript to a level that confers a therapeutic effect. Delivery of an RNAi-inducing agent suitably reduces expression of the target transcript at least about 25%, at least about 50%, at least about 80%, at least about 90%, at least about 95%, at least about 98%, at least about 99% or 100%, relative to expression of the transcript in an appropriate control cell. The percentage reduction in expression can be calculated by the following equation:

$$[(\text{Expression target transcript in sample} - \text{Expression of target transcript in control})/\text{Expression target transcript in sample}] \times (-100)$$

Specifically contemplated RNAi inducing agents include short interfering RNA ("siRNA"), short hairpin RNA ("shRNA"), and RNAi-inducing vectors, each of which is defined below. Selection of appropriate target sequences for RNAi may take into account factors such as synthetic considerations, avoidance of targeting unwanted transcripts, and other considerations, as described by Manoharan, Current Opinion in Chemical Biology, 8:570-579 (2004), which is incorporated herein by reference in its entirety.

A "short, interfering RNA," or "siRNA," comprises an RNA duplex that is about 19 to about 27 base pairs in length and optionally further comprises one or two single-stranded overhangs. siRNA can be chemically synthesized, or can be transcribed in vitro from a DNA template, or in vivo from an RNA precursor. An siRNA may be formed from two RNA molecules that hybridize, or may alternatively be generated from a single RNA molecule that includes a self-hybridizing portion. It is generally preferred that free 5' ends of siRNA molecules have phosphate groups, and free 3' ends have hydroxyl groups. The duplex portion of an siRNA may, but typically does not, contain one or more unpaired nucleotides. One strand of an siRNA includes a portion that hybridizes with a target transcript. In certain embodiments of the invention, one strand of the siRNA is precisely complementary with a region of the target transcript, meaning that the siRNA hybridizes to the target transcript without a single mismatch. In other embodiments, one or more mismatches between the siRNA and the targeted portion of the target transcript may exist. In most embodiments of the invention in which perfect complementarity is not achieved, it is generally preferred that any mismatches be located at or near the siRNA termini. An siRNA used in accordance with the invention is suitably hybridizable to a target transcript and capable of inducing its degradation.

The term "short hairpin RNA" refers to an RNA molecule comprising at least two complementary portions hybridized or capable of hybridizing to form a double-stranded (duplex) structure of sufficient length to mediate RNAi (typically about 19-27 base pairs in length), and at least one single-stranded portion, typically between approximately 1 and 10 nucleotides in length, that forms a loop structure. The duplex portion may, but typically does not, contain one or more unpaired nucleotides. Not to be bound by theory, it is thought that shRNAs are precursors of siRNAs and are, in general, similarly capable of inhibiting expression of a target transcript.

As used herein, "an RNAi-inducing vector" is a vector whose presence within a cell results in transcription of one or more RNAs that self-hybridize or hybridize to each other to form an shRNA or siRNA. The term generally encompasses any construct comprising a polynucleotide operably linked to expression signal(s) so that one or more RNA molecules that hybridize or self-hybridize to form an siRNA or shRNA are transcribed when the vector is present within a cell. Thus, the vector provides a template for intracellular synthesis of the RNA-inducing agent or precursors thereof. An RNAi-inducing vector is considered to be targeted to a transcript if presence of the vector within a cell results in production of one or more RNAs that hybridize to each other or self-hybridize to form an siRNA or shRNA that is targeted to the transcript, i.e., if presence of the vector within a cell results in production of one or more siRNAs or shRNAs targeted to the transcript. Genetic constructs for the delivery of siRNA molecules are described, for example, in U.S. Pat. No. 6,573,099, which is incorporated herein by reference. A further example of the use of shRNA expression plasmids to reduce gene expression in vivo in rats has been described by Zhang et al. (J. Gene Med. 5:1039-1045, 2003), which is also incorporated herein by reference.

In particular embodiments, the RNAi-inducing agent is suitably stabilized by chemical modification. For example, siRNAs may be crosslinked to increase half-life in the body. For example, a 3' OH terminus of one of the strands of double-stranded siRNA can be modified, or the two strands can be crosslinked and modified at the 3' OH terminus. The siRNA derivative can contain a single crosslink or multiple crosslinks. Additionally, stability may be enhanced by including nucleotide analogs at one or more free ends in order to reduce digestion, e.g., by exonucleases. The inclusion of deoxynucleotides, e.g., pyrimidines such as deoxythymidines at one or more free ends, may serve this purpose. It will further be appreciated by those of ordinary skill in the art that effective siRNA agents for use in accordance with certain embodiments of the invention may comprise one or more moieties that are not nucleotides or nucleotide analogs. Further suitable chemical modifications are described by, e.g., Manoharan, Current Opinion in Chemical Biology, 8:570-579 (2004), incorporated herein by reference in its entirety.

In a further embodiment, micro RNA ("miRNA") may be delivered to cells according to the invention. As used herein, "micro RNA" or "miRNA" refers to single-stranded, non-coding RNA molecules of about 19 to about 27 base pairs which regulate gene expression in a sequence specific manner.

In another embodiment of the invention, an antagomir is delivered to cells according to the invention. As used herein, an "antagomir" is an RNA species that is complementary to an endogenous target miRNA. Suitably, upon binding of an antagomir to its complement miRNA, the action of the miRNA is antagonized.

In yet another embodiment, a cytotoxic moiety may be delivered to cells according to the invention. A "cytotoxic moiety," as used herein, refers to any agent which induces apoptosis, anoikis or necrosis in cells to which the cytotoxic moiety is delivered. In the context of ovarian, breast or prostate cancers, ribosome inactivating proteins such as (1) the fungal ribonuclease toxins such as restrictocin and α-sarcin, and (2) deglycosylases such as gypsophilin and ricin, may be particularly suitably delivered. Other suitable cytotoxic moieties include particular chemotherapeutic moieties, as described below.

A "chemotherapeutic moiety," as used herein, refers to any agent which interferes with cell division, disrupts normal functionality of microtubules, inhibits utilization of a metabolite, substitutes nucleotide analogs into cellular DNA, or inhibits enzymes which are necessary for DNA replication, RNA transcription or protein translation. As will be appreciated, any chemotherapeutic moiety may be delivered. However, carboplatin, Paclitaxel, Docetaxel, Adriamycin, 5-Fluorouracil and small molecule inhibitors may be particularly well suited for delivery in the context of ovarian, breast or prostate cancers which express or overexpress prolactin receptors.

Radioactive moieties are also suitably delivered by way of the invention. As used herein, a "radioactive moiety" can include any chemical entity that comprises an unstable isotope, i.e., a radionuclide. Suitable radionuclides include both alpha- and beta-emitters. In some embodiments, the receptor ligand is radiolabelled. In other embodiments, suitable radioactive moieties include radiolabelled polynucleotides and polypeptides which can be coupled to the prolactin receptor ligand receptor ligand. Radionuclides emitting low-energy electrons (e.g., those that emit photons with energies as low as 20 keV) are particularly suitable for particular embodiments of the invention because they can irradiate the cell to which they are delivered without irradiating surrounding cells or tissues. Non-limiting examples of radionuclides that are suitably delivered to cells in accordance with the invention include $^{137}$CS, $^{103}$Pd, $^{111}$In, $^{125}$I, $^{211}$At, $^{212}$Bi and $^{213}$Bi, among others known in the art.

Imaging moieties are also suitably delivered to a cell comprising a receptor according to the invention. As used herein, an "imaging moiety" is any entity which enhances visualization or detection of the cell to which it is delivered. In some embodiments, the imaging moiety is selected from a radioisotope for nuclear imaging, a paramagnetic species for use in MRI imaging, an echogenic entity for use in ultrasound imaging, a fluorescent entity for use in fluorescence imaging, and a light-active entity for use in optical imaging. Specific non-limiting examples of fluorophores that may be delivered to a cell include e.g., Cy3, fluorescein and rhodamine. A suitable species for MRI imaging is a gadolinium complex of diethylenetriamine pentacetic acid (DTPA). For positron emission tomography (PET), $^{18}$F or $^{11}$C is suitably delivered.

In a further embodiment, the invention suitably delivers a nanoparticle to a cell. As used herein and in the art, a "nanoparticle" refers to a submicrometer-scale delivery vehicle having a cytotoxic, chemotherapeutic and/or imaging agent encapsulated therein. Particularly suitable nanoparticles for therapeutic applications will be biodegradable, such that the encapsulated agent is released into the interior of the cell upon internalization. In one suitable formulation, the nanoparticles have three modules: (1) a core domain for packaging the chemotherapeutic and/or imaging agent; e.g. polyethylene imine (PEI) for packaging siRNA, (2) a steric coating such as polyethylene glycol (PEG) for protection of the core, and (3) surface exposed prolactin receptor ligand(s). Some of the PEG-core domain fusions in the nanoparticle may bear the prolactin receptor ligand. Schiffelers et al., Nucleic Acids Res. 32(19):e149 (2004), incorporated herein by reference in its entirety, generally describes siRNA delivery using nanoparticles, and such methods may be adapted for use with the present invention.

In other embodiments, a polynucleotide comprising a sequence encoding a polypeptide operably linked to a promoter may be delivered to cells according to the methods of the invention. The polynucleotides may be provided as linear double-stranded DNA, or may be associated with vectors, e.g., plasmid vectors. Expression of the polypeptide within the cell suitably results in a therapeutic effect. In particular embodiments, the polynucleotide encodes a polypeptide that may be particularly well suited for delivery in the context of ovarian, breast or prostate cancers. For example, suitable polynucleotides encode e.g., p53, p16, TIMP-1, TIMP-2, PAI-1, Rb, TGFβ, p21, Factor VII, Factor VII, caspase 8, and E-cadherin.

Ligand-Agent Coupling

As noted, a cell expressing a prolactin receptor is contacted with a complex of the agent and the prolactin receptor ligand such that endocytosis is triggered and the agent is taken up by the cell. In particular embodiments, the agent and ligand are coupled by means of suitable coupling chemistry. In other embodiments, the complex is prepared by recombinant methods to produce, e.g., a fusion polypeptide of both entities.

Suitable means of coupling an agent to a ligand are known in the art, as described in, e.g., Bioconjugate Techniques, Greg T. Hermanson (1996) Academic Press, San Diego, incorporated herein by reference. Disulfide coupling using cysteine residues outside the binding domain of the receptor ligand is one particularly suitable coupling strategy. In particular embodiments, one or more cysteine residues may be introduced in the receptor ligand using standard techniques to facilitate coupling to the agent to be delivered. In some embodiments, the coupling strategy is chosen to facilitate release of the agent from the receptor ligand upon uptake by the cell, however, in other embodiments, this is not necessary to achieve the desired effect.

In one suitable formulation, SPDP (N-succinimidyl 3-(2-pyridyldithio)propionate, a commercially available, heterobifunctional cross-linking reagent, is used to couple a nucleic acid agent to a prolactin receptor ligand. One end of SPDP contains an activated N-hydroxysuccinimide (NHS) ester, which reacts with alkyl amine groups to form an amide linkage. The other end of SPDP contains a 2-pyridyldithiol group, which reacts with sulfhydryl groups (—SH) to form a disulfide linkage. The nucleic acid agent is suitably prepared to provide a hexylamine moiety at one of its termini. Conjugation to the receptor ligand suitably occurs in two stages. In the first stage, the hexylamine group reacts with the NHS moiety of SPDP to form a nucleic acid-SPDP conjugate. In the second stage, the 2-pyridyldithiol group of this conjugate reacts with a cysteine residue in the prolactin receptor ligand via thiol disulfide exchange chemistry, generating the prolactin receptor ligand-nucleic acid conjugate.

In a second suitable strategy, a different heterobifunctional cross-linking reagent, SMCC (succinimidyl 4-(N-maleimidomethyl)cyclohexane-1-carboxylate), is used. Like SPDP, one end of SMCC contains an activated NHS ester, but the other end contains a maleimide group, which reacts with thiols. The strategy for coupling this reagent parallels the SPDP-based strategy described above. In stage 1, the NHS ester reacts with the hexylamine-containing nucleic acid, and in stage two, the resulting nucleic acid-SMCC conjugate reacts with a cysteine residue in the receptor ligand. In the SPDP linked conjugate, the prolactin receptor ligand is attached to the nucleic acid via a disulfide bond, which may be reduced in the cellular environment. In the SMCC linked conjugate, the ligand is attached to the nucleic acid via a thioether linkage, which is inert under physiological conditions.

In addition to the disulfide exchange chemistry and maleimide strategies described above, there are numerous other chemistries that are suitable for coupling agents to receptor ligands, including, but not limited to: haloacetyl and alkyl halide derivatives, aziridines, acryloyl derivatives and arylating agents. In principle, any one of these strategies could be used to link agents of interest to the receptor ligand.

In a further embodiment, the complex is a fusion polypeptide. The fusion polypeptide includes the sequence of an agent and the sequence of the receptor ligand. Suitably, the sequence of the agent and the sequence of the receptor ligand are connected by a linker sequence. Suitably, the agent may be a cytotoxic moiety, for example, restrictocin. The fusion protein may be produced by methods known in the art, e.g., molecular cloning and protein expression. A suitable method of producing a fusion peptide is described in the Examples below.

Methods of Use

The invention provides for methods of inhibiting expression of an mRNA in a cell comprising a prolactin receptor, comprising contacting the cell with a complex comprising an RNAi-inducing agent coupled to a prolactin receptor ligand, wherein the RNAi-inducing agent is complementary to at least a portion of the mRNA. Suitably, the RNAi-inducing agent is complementary to about 19 to about 27 consecutive nucleotides of the mRNA. In particular embodiments, delivery of an RNAi-inducing agent reduces expression of the mRNA at least about 25%, at least about 50%, at least about 80%, at least about 85%, at least about 90%, at least about 95%, at least about 98%, at least about 99% or 100%, relative to expression of the mRNA in an appropriate control cell. An example of an appropriate control is a cell that has not been contacted with the complex, or has been contacted with a complex comprising a prolactin receptor ligand coupled to an irrelevant siRNA. The percentage of reduction of expression of the mRNA may be calculated using the following equation:

[Expression target mRNA in sample−Expression target mRNA in control)/Expression target mRNA in sample]×(−100)

Suitably, the RNAi-inducing agent is an siRNA. In general, the target mRNA can be any mRNA molecule within the cell.

As will be appreciated, where a disease or symptom is associated with excessive or inappropriate expression of a polypeptide, e.g., an enzyme or receptor, a particularly effective strategy is to target mRNA transcripts for the excessively or inappropriately expressed polypeptide. In other embodiments, it may be effective to target mRNA transcripts for a polypeptide exhibiting inappropriate activity.

Suitably, the target mRNA encodes a cell surface receptor. In particular embodiments, the cell surface receptor comprises c-Met, any member of the EGF receptor family, PDGFR, VEGFR or the transferrin receptor. In other embodiments, the mRNA encodes a protease or its receptor, e.g., urokinase (or a urokinase-type plasminogen activator, or urokinase-type plasminogen activator receptor) or a member of the matrix-metalloproteinase family. In further embodiments, the mRNA encodes a signal transduction molecule, e.g., Stat-3, Stat-5, Erk1, Erk2, Jnk1, Jnk2, p38, Erk5, Akt, c-Kit, a PI3 kinase subunit or ATM. In still further embodiments, the mRNA encodes a transcription factor, e.g., HIF-1 with its subforms, HIF-2, c-Jun, JunD, p53 or the estrogen receptor. In additional embodiments, the mRNA encodes a cell cycle regulator, e.g., cyclin D1, cyclin D2, cyclin D3, cyclin E, cdc2, cdk2 or cdk4. Suitably, multiple mRNAs may be selected to enhance silencing of a particular target, e.g., transcripts for multiple effectors within a given biochemical pathway can be selected such that one or more end products of the pathway is more effectively inhibited.

As will be appreciated, the ability of a candidate RNAi-inducing agent to reduce the level of the target transcript may be assessed by measuring the amount of the target transcript using, for example, Northern blots, nuclease protection assays, reverse transcription (RT)-PCR, real-time RT-PCR, microarray analysis, etc. The ability of a candidate RNAi-inducing agent to inhibit expression of a polypeptide encoded by the target transcript (either at the transcriptional or post-transcriptional level) may be measured using a variety of approaches, e.g., antibody-based approaches including, but not limited to, Western blots, immunoassays, flow cytometry, protein microarrays, etc.

In further embodiments, the invention also provides methods of inhibiting a cancer cell comprising a prolactin receptor, comprising contacting the cell with a complex comprising prolactin receptor ligand linked to at least one of a RNAi-inducing agent, a polynucleotide sequence encoding a polypeptide, an miRNA, a cytotoxic moiety, a chemotherapeutic moiety, a radioactive moiety or a nanoparticle. In some embodiments, the cancer cell overexpresses prolactin receptor. As used herein, "inhibiting a cancer cell" refers to any of: 1) inducing apoptosis or anoikis of the cancer cell, 2) inducing necrosis of the cancer cell, or 3) preventing proliferation of the cancer cell. Suitably, the cancer cell is a breast cancer cell, an ovarian cancer cell or a prostate cancer cell. Accordingly, the invention provides an effective strategy to treat cancer, e.g., ovarian cancer, breast cancer or prostate cancer. As used herein, "treating" or "treatment" of a cancer in a mammal includes one or more of: 1) inhibiting growth of the cancer, i.e., arresting its development, 2) preventing spread of the cancer, i.e., preventing metastases, 3) relieving the cancer, i.e., causing regression of the cancer, 4) preventing recurrence of the cancer, and 5) palliating symptoms of the cancer. "Treatment" refers to therapy, prevention and prophylaxis, and more particularly, refers to the administration of medicine or other modality or to the performance of medical procedures with respect to a patient, for either prophylaxis or to cure or reduce the extent of or likelihood of occurrence of the condition of which the patient is afflicted.

An additional embodiment of the invention provides a method of detecting a cancer cell comprising a prolactin receptor. The cancer cell is suitably an ovarian cancer cell, a breast cancer cell or a prostate cancer cell that overexpresses prolactin receptor. The method includes contacting a tissue suspected of comprising a cancer cell with a complex comprising a prolactin receptor ligand coupled to a detectable marker, detecting levels of the marker present in the tissue, and correlating elevated levels of marker relative to control tissue with the presence of a cancer cell in the tissue. Any suitable mode of detection may be employed, depending on the detectable marker used. The method may be adapted for use in vitro or in situ.

Compositions

The complex of the invention is suitably included in a pharmaceutical composition in a therapeutically effective amount. Such compositions typically include the complex and a pharmaceutically acceptable carrier. As used herein, "pharmaceutically acceptable carrier" includes saline, solvents, dispersion media, coatings, antibacterial and antifungal agents, isotonic and absorption delaying agents, and the like, compatible with pharmaceutical administration.

As appreciated by skilled artisans, pharmaceutical compositions are suitably formulated to be compatible with the intended route of administration. Examples of suitable routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH of the composition can be adjusted with acids or bases, such as hydrochloric acid or sodium hydroxide. Systemic administration of the complex is also suitably accomplished by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Toxicity and therapeutic efficacy of pharmaceutical compositions comprising the complexes of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices are preferred. As will be appreciated by skilled artisans, data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

As will be appreciated, a therapeutically effective amount of the complex of the invention will depend on the agent selected. The skilled artisan will appreciate that certain factors may influence the dosage and timing required to effectively treat a subject, including but not limited to the severity of the disease or disorder, previous treatments and the general health and/or age of the subject. Therapeutically effective amounts may be determined by the skilled practitioner. Treatment of a subject with a therapeutically effective amount of a complex of the invention can be accomplished in a single treatment or, preferably, can include a series of treatments.

It is specifically contemplated that any embodiment of any method or composition of the invention may be used with any other method or composition of the invention.

As used in this specification and the appended claims, the singular forms "a," "an," and "the" include plural referents unless the content clearly dictates otherwise. Thus, for example, reference to a composition containing "a virus" includes a mixture of two or more viruses. It should also be noted that the term "or" is generally employed in its sense including "and/or" unless the content clearly dictates otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

EXAMPLES

The following examples are provided to assist in a further understanding of the invention. The particular materials and conditions employed are intended to be further illustrative of the invention and are not limiting on the reasonable scope of the appended claims.

Example 1

Characterization of c-Met Expression in Ovarian Cancer Cell Lines

Expression of c-Met was characterized in ovarian cancer samples by immunohistochemistry and immunofluorescence.

Tissue blocks from 161 patients with FIGO stage III/IV advanced ovarian or peritoneal cancer who had undergone tumor debulking by a Gynecologic Oncologist at the Section of Gynecologic Oncology at the University of Chicago between 1994-2004 were selected for the study after IRB approval was obtained. Samples of tissue sections from the primary tumors were stained with hemotoxylin and eosin (H&E) and a pathologist outlined the areas to be punched. 1.5 mm cores of tissue were punched from donor blocks and inserted into a recipient block. The tissue micro array (TMA) was cut in 5 μm sections and stained with H&E to confirm the presence of tumor. Satisfactory immunohistochemical staining of c-Met was obtained in 138 patients. A detailed Microsoft Access database (Version 2003-SP2) was designed and demographic and histopathologic data entered according to the WHO classification of ovarian cancer. Follow-up information was gathered by reviewing the hospital and outpatient clinic charts, data from the Illinois Cancer Registry, the U.S. Social Security Index, and by contacting physicians involved in the patient's care.

TMA slides were deparaffinized in xylene and hydrated with alcohol before being placed in 3% $H_2O_2$/methanol blocking solution, which was followed by antigen unmasking. Incubation with the primary antibody against total c-Met (3D4) was done with a 1:100 dilution. After washing, the slides were stained using the Envision avidin-biotin-free detection system (DAKO, Carpenteria, Calif.) and counterstained with hematoxylin. Appropriate negative controls were prepared by omitting the primary antibody step and substituting it with non-immune rabbit serum. (See FIG. 1A).

The slides were reviewed manually by two independent pathologists. Immunoscoring was done using the Automated Cellular Imaging System, ACIS (Clarient, Calif.). Within the tissue core, the most representative tumor area of standardized size was selected at 100× magnification. The staining intensity in this area was measured if the area contained more than 5% epithelial cells. Stains were scored as negative (−), weak (+), intermediate (++), and strongly positive (+++).

As shown in FIGS. 1B-1C, samples of serous ovarian cancers were found to stain positively for c-Met as compared to negative controls. As shown in FIG. 1D, analysis of c-Met expression showed that overexpression of c-Met correlates with an adverse outcome.

Example 2

Figure 8:
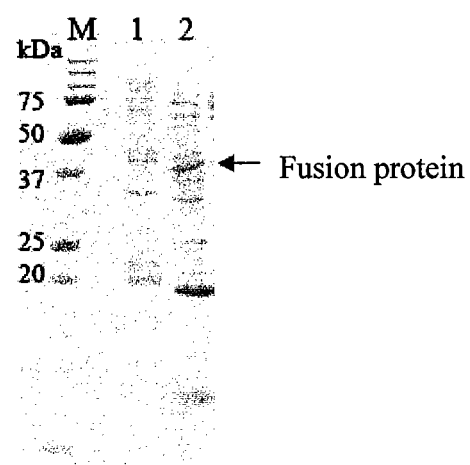
FIG. 8 is an image of a coomassie blue stained gel used to resolve the purified restrictocin-hPL fusion protein.

Characterization of hPRL Receptor Expression in Ovarian and Breast Cancer Cell Lines To validate the human prolactin receptor (hPRLR) as a target receptor in ovarian cancer, we characterized its expression in ovarian cancer cell lines, a breast cancer cell line and ovarian cancer tissue. Quantitative real time (RT)-PCR analysis was used to determine expression of hPRLR with a PRLR Taq Man probe. As shown in FIG. 2A, 8 out of 10 ovarian cell lines, as well as the breast cancer cell line MCF-7, express hPRLR mRNA.

Human prolactin receptor was also detected by immunohistochemistry using an anti-hPRLR monoclonal antibody. Slides were reviewed manually by two independent pathologists. Immunoscoring was done as described in Example 1 using the Automated Cellular Imaging System, ACIS (Clarient, Calif.). 80% of ovarian cancer cell lines expressed the hPRLR protein. (Representative stainings shown in FIG. 2B). As shown in FIG. 2B, the hPRLR is localized both in the cytoplasm and in the nucleus of the ovarian cancer and normal surrounding tissue does not express hPRLR.

Example 3

Internalization of a c-Met siRNA Conjugated to FITC in CaOV3 Cells

Figure 3:
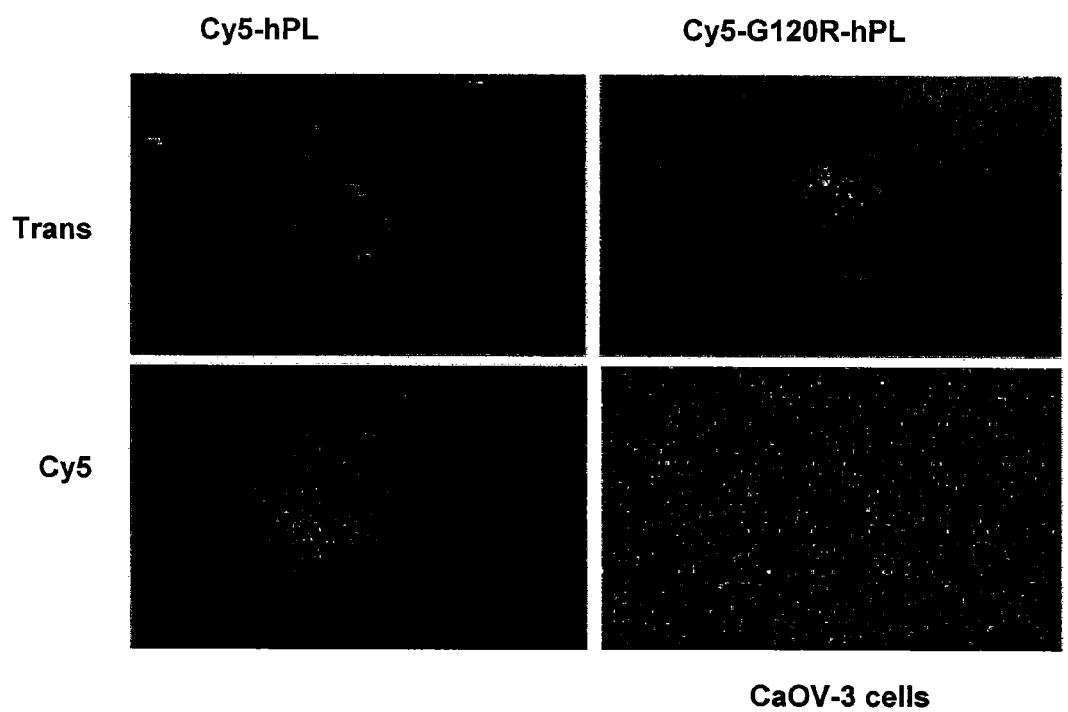
FIG. 3 shows fluorescent microscopy images of CaOV-3 cells treated with Cy5-conjugated human placental lactogen (Cy5-hPL) or a Cy-5-conjugated hPL mutant (Cy5-G120R-hPL).

CaOV-3 cells were plated and treated with a Cy5-conjugated hPL or a Cy-5-conjugated hPL mutant (G120R). Internalization of the conjugates was examined using confocal microscopy. As shown in FIG. 3, the hPL conjugate was internalized, but the mutated form, which cannot bind the dimerized hPRLR, was not internalized.

Example 4

Construction of an hPL/c-Met siRNA Conjugate

A 21-mer double-stranded RNA was covalently linked to hPL via disulfide bond exchange of SPDP-derivatized dsRNA with cysteine 138 of hPL. Strand 1 of the c-Met 21-mer oligonucleotide duplex (N6-CUG UCA GAG GAU ACU GCA CUU-3'FITC) (SEQ ID NO:1) contains a hexylamine linkage at its 5'-terminus (N6) and FITC at its 3'-terminus. This oligonucleotide was ethanol precipitated, resuspended and derivatized with N-succinimidyl-3-(2-pyridyldithio)-propionate (SPDP). The SPDP derivatized oligonucleotide was separated from the underivatized oligonucleotide using reverse phase HPLC. This RNA was hybridized to strand 2 in a 1:1 ratio. Before conjugation, hPL protein was reduced with 10 equivalents of TCEP (tris(2-carboxyethyl-phosphine) or DTT prior to the addition of the SPDP derivatized dsRNA.

Figure 13:
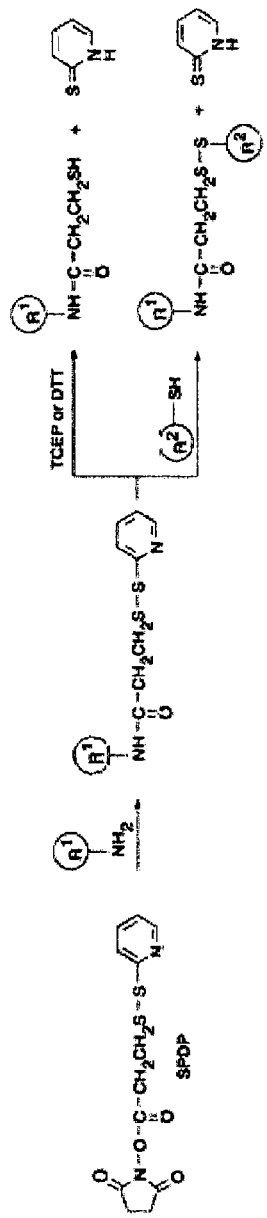
FIG. 13 depicts a reaction scheme for coupling a c-Met RNA and hPL by disulfide bond exchange of SPDP-derivatized dsRNA with cysteine 138 of hPL, where R1 is c-Met siRNA-labeled with FITC and R2 is I138C-hPL.

The reaction scheme is shown in FIG. 13 (where R1 is c-Met siRNA-FITC and R2 is I138C-hPL).

Example 5

Specificity of c-Met siRNA Covalently Coupled to hPL for Cancer Cells Versus Normal Cells Normal human peritoneal mesothelial cells were obtained from surgery and co-cultured with human CaOV-3 ovarian cancer cells. Cells were treated with DAPI, fluorescently-labeled hPL-cMet siRNA and a rhodamine-coupled anti-hPRL receptor antibody. Stained cells were visualized using fluorescence and confocal microscopy.

Figure 4:
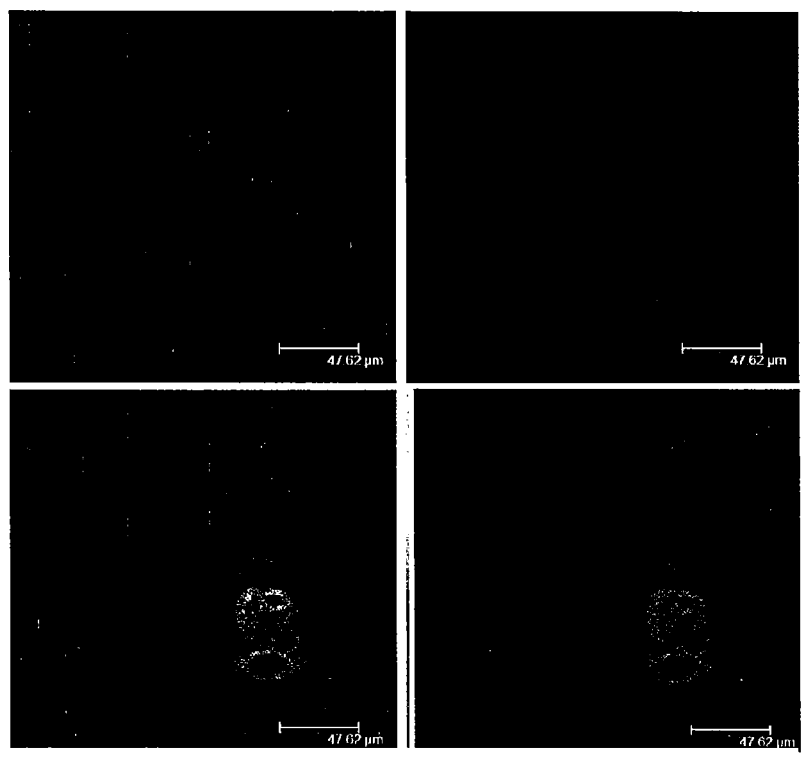
FIG. 4 shows comparative staining for cell nuclei and prolactin receptor in co-cultured ovarian cancer and normal human peritoneal mesothelial cells.

As shown in FIG. 4, top left panel, both human peritoneal mesothelial cells and CaOV-3 cells stain with DAPI. As shown in FIG. 4, top right panel, CaOV-3 cells, but not peritoneal cells, stained for the human prolactin receptor with the rhodamine-coupled antibody. As shown in FIG. 4, bottom right panel, CaOV-3 cells, but not peritoneal cells, stained with the hPL c-Met siRNA. The bottom left panel of FIG. 4 shows superimposed images. These results show that there is a direct correlation between cancer cells and cells susceptible to delivery by hPL-coupled agents. The results also show that normal cells are not susceptible to delivery.

Example 6

Inhibition of Expression of c-Met with c-Met siRNA Covalently Coupled to hPL

Human placental lactogen (hPL), a homolog of PRL, was coupled to an siRNA designed to silence the c-Met receptor as described in Example 4. c-Met is a receptor of the tyrosine kinase family that mediates the diverse activities of its ligand, hepatocyte growth factor (HGF), which is a growth and mitogenic factor. HGF induces autophosphorylation of c-Met generating phosphotyrosine docking sites for adaptor proteins (Gab-1, Grb2, Shc), which in turn activate signal transduction pathways such as PI3K, STATs, Erk1, paxillin and FAK, all of which have been implicated in tumor progression.

$5 \times 10^5$ CaOV-3 ovarian tumor cells and MCF-7 breast cancer cells were plated. 24 hours later after plating, cells were treated with 0.5 μg/ml hPL-c-Met siRNA. At time points indicated in FIG. 5, 15 μg of cell extracts were separated by 10% SDS-PAGE, transferred to a membrane and probed using an anti-human c-Met antibody.

Figure 5:
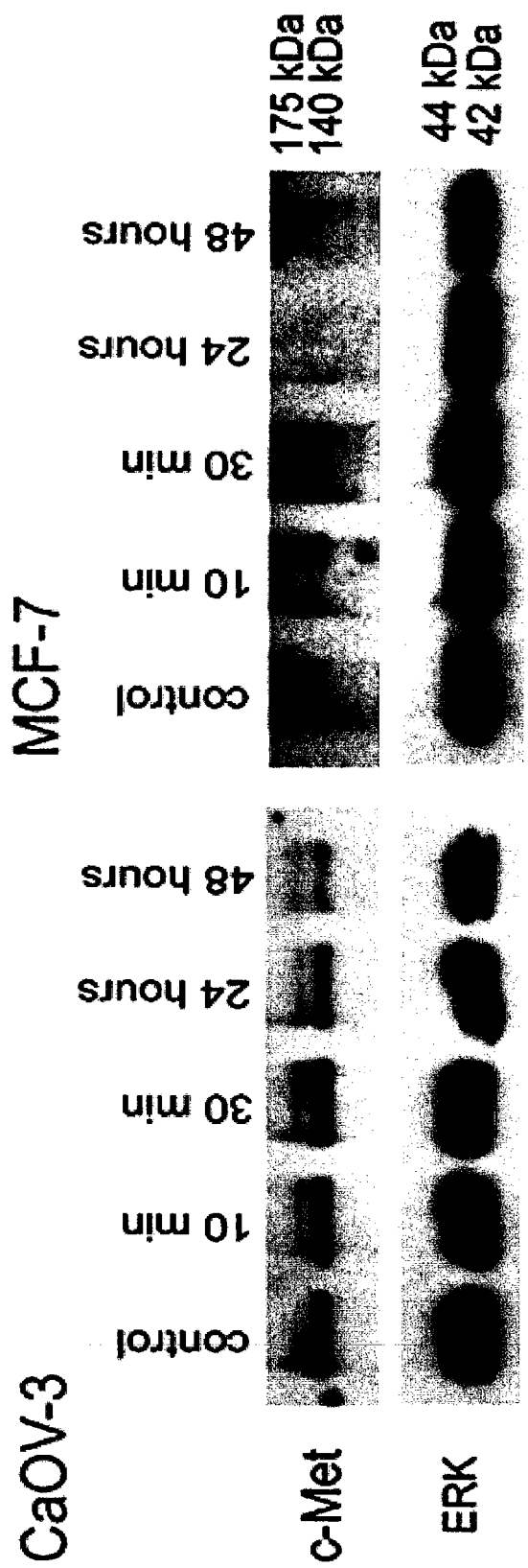
FIG. 5 shows photos of immunoblots of ovarian cancer and breast cancer cell extracts taken at various time points showing inhibition of c-Met protein expression by an hPL-c-Met siRNA conjugate.

As shown in FIG. 5, the hPL-c-Met conjugate inhibited c-Met expression in CaOV-3 and MCF-7 cells. As determined by image analysis, c-Met expression was reduced >90%.

Example 7

Restrictocin-hPL Conjugate Preparation and Internalization

Fluorescently-labeled restrictosin was conjugated to hPL and the ability of this complex to internalize into cells expressing the prolactin receptor was tested by confocal microscopy and western blotting.

Restrictocin dissolved in 10 mM Tris-HCl, pH 7.5, 1 mM $MgCl_2$ was dialyzed into PBS 7.1 overnight at 4° C., and then diluted in PBS to a final concentration of 5 mg/ml. A 1:1 molar ration of restrictocin to rhodamine green was incubated at room temperature for 120 minutes. Excess fluorophore was removed using filter centrifugation (Microcon YM-10 centrifugal filters, MWCO-10,000 Da).

Figure 9:
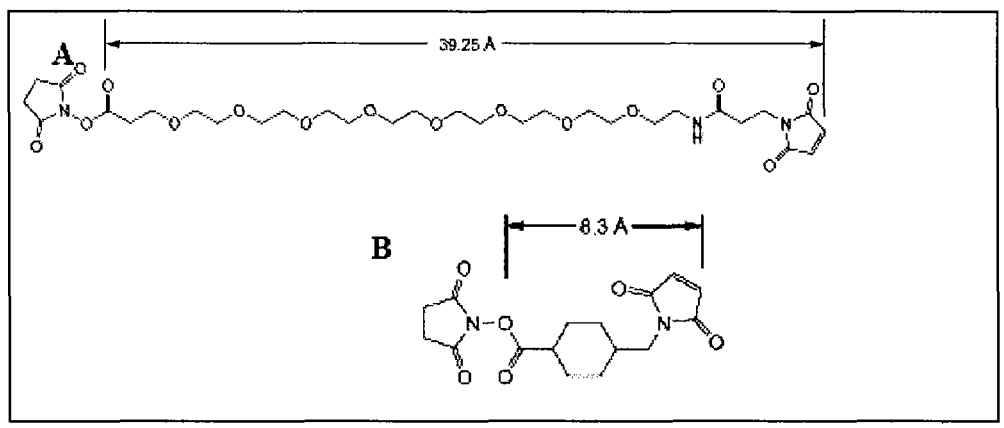
FIG. 9A depicts the cross-liker SMCC (succinimidyl 4-(N-maleimidomethyl)cyclohexane-1-carboxylate) and FIG. 9B depicts the crosslinker NHS-PEO$_8$-Malenimide(succinimidly-[(N-maleimido-propionamido)octaethyl-enegylcol]ester).
Figure 10:
FIG. 10 is a schematic drawing of the restrictocin-hPL fusion protein.
Figure 11:
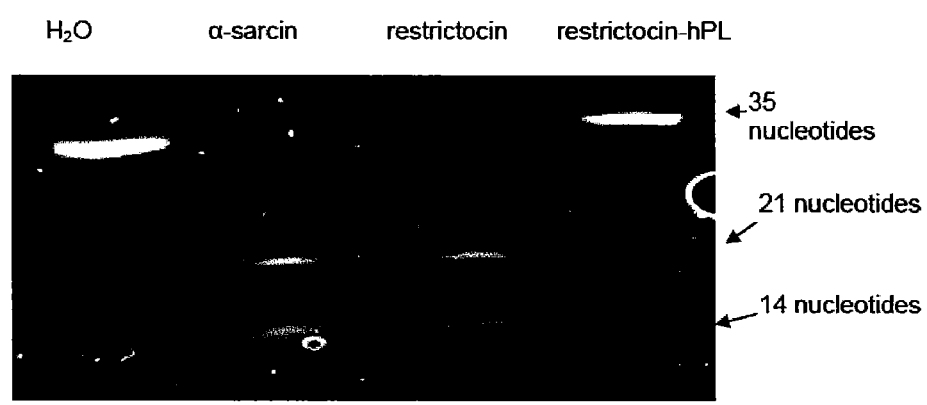
FIG. 11 is an image of a gel comparing the RNA cleavage capabilities of E1 rat RNA by α-sacrin, restrictocin, and restrictocin-hPL conjugate.
Figure 12:
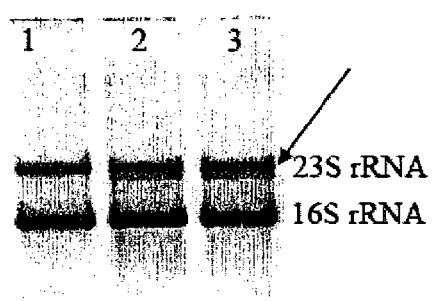
FIG. 12 is an image of a gel comparing levels of rRNA cleavage by restrictocin and restrictocin-hPL conjugate.

The rhodamine green labeled restrictocin was diluted to a 0.1 mM concentration in conjugation buffer (PBS, pH 7.2 or PBS $NaHCO_3$ pH 8.3) and reacted with 2-fold molar excess (0.2 mM final concentration) of heterobifunctional crossliker NHS-$PEO_8$-Malenimide (succinimidly-[(N-maleimidopropionamido)-octaethylenegylcol]ester) (FIG. 9B) or SMCC (succinimidyl 4-(N-maleimidomethyl)cyclohexane-1-carboxylate) (FIG. 9A). Crosslinkers were dissolved in DMSO, and reacted with the toxin for 30 minutes at room temperature with shaking. Excess cross-linker was removed by filter centrifugation.

Recombinant hPL having an I138C mutation and a 6HIS-tag ("I138C-hPL-6His-tag") was reduced using 10 fold excess of TCEP for one hour at room temperature. TCEP was removed from the mixture using ZEBRA desalting spin columns and dialyzed into PBS pH 7.2. The rhodamine green-restrictocin-cross-linker conjugate was reacted with I138C-hPL-6His-tag (after reduction with TCEP) in PBS, pH 7.2, overnight at 4° C. at a molar ratio of 0.9:1 hPL to toxin. The product of the conjugation reaction was purified by filter centrifugation.

To prepare the negative control, 10 mg/ml BSA in 50 mM Tris-HCl, pH 7.5 was reduced using 10 fold molar excess TCEP for 1 hour at room temperature, and TCEP was removed using ZEBRA desalting spin columns, dialyzed into PBS pH 7.2 and crosslinked to labeled restrictocin as described above for hPL.

A 1 ml nickel affinity column was used to purify the rhodamine green labeled-restrictocin hPL-6-His tag conjugate and rhodamine green labeled-restrictocin-BSA conjugates.

Figure 6:
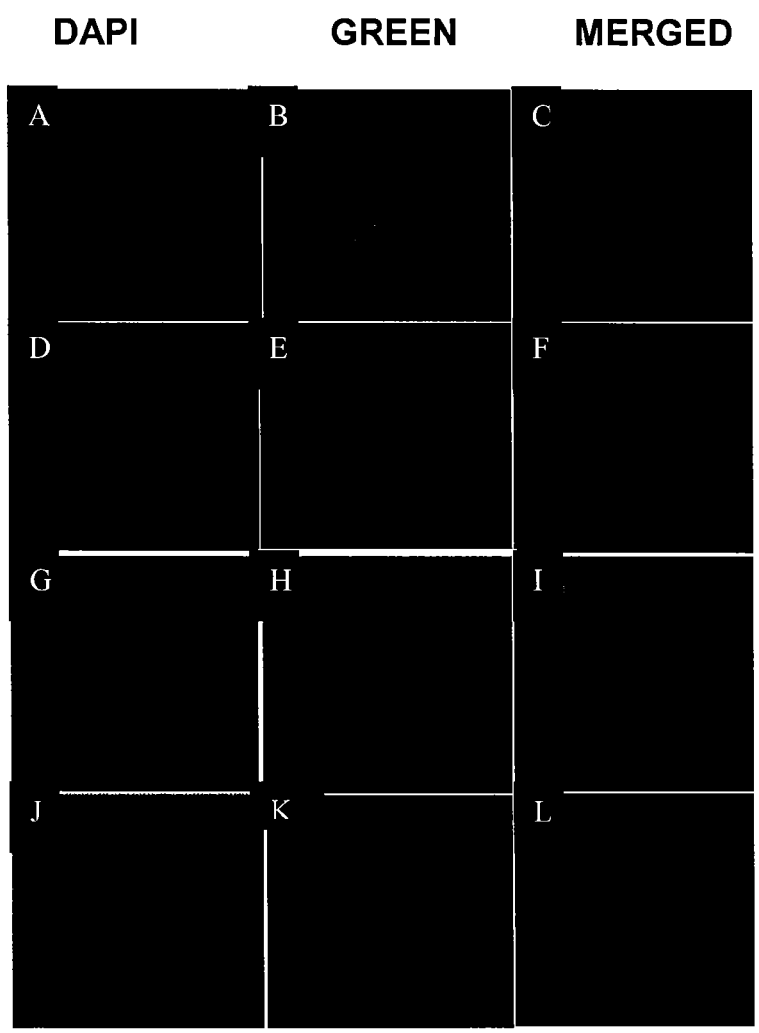
FIGS. 6 A-L are confocal microscopy images showing internalization of fluorescently coupled hPL-siRNA conjugates.

To test for internalization of the conjugate, T47D cells (cells that overexpess the prolactin receptor) and SKOV-3 cells (negative control cells that have low expression of the prolactin receptor) were incubated with 0.2 μM restrictocin-hPL conjugate, restrictocin-BSA conjugate, or 5-IAF-hPL (IAF-labeled hPL is used as a positive control for receptor-uptake through prolactin receptors) for 1 hour at 37° C. The cells were acid-washed, fixed and stained with DAPI to visualize cell nuclei. As seen in FIG. 6, the restrictocin-hPL conjugate was internalized in the T47D cells (FIG. 6B) but not the SKOV-3 cells (FIG. 6H). The BSA-restrictocin conjugate was also not able to be internalized into the T47D cells as seen in FIG. 6K. Therefore, restrictocin enters T47D cells in a receptor-dependent manner.

Figure 7:
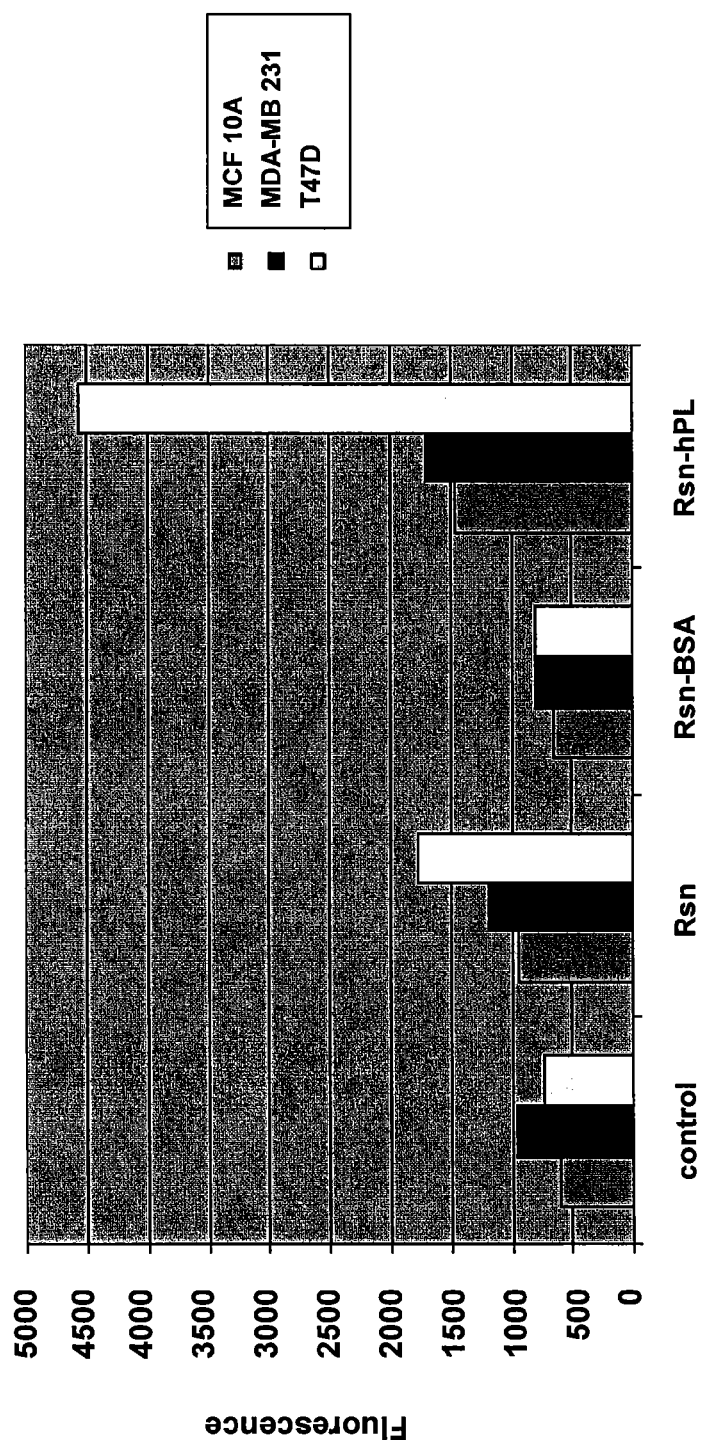
FIG. 7 is a bar graph representing the number of cells that emit fluorescence after treatment with restrictocin (rsc), restrictocin conjugated to BSA (Rsn-BSA), or restrictocin conjugated to hPL (Rsn-hPL) in MCF 10 A, MDA-MB 231 and T47D cells.

To confirm that the restrictocin-hPL conjugate is delivered to cells specifically and that internalization depends on the prolactin receptor, three cell lines, T49D (overexpressed prolactin receptor), MCF 10A and MDA-MB 231 (both do not overexpress prolactin receptor), were incubated with 0.2 μM restrictocin-BSA conjugate or 0.2 μM rhodamine green-restrictocin-hPL conjugate for 1 hour at 37° C. Uptake of restrictocin was measured by flow cytometry. A decrease in fluorescence was observed in samples in which cells were incubated with restrictocin-BSA conjugate compared to cells incubated with restrictocin alone as seen in FIG. 7. An increase in fluorescence was only seen in T47D cells that overexpress the prolactin receptor as seen in FIG. 7. These results show that internalization of restrictocin-hPL conjugate is dependent on hPL/prolactin receptor endocytosis.

Example 8

Restrictocin-hPL Cleavage of Ribosomes

E1-RNA and Ribosome cleavage assays were used to determine the ability of restrictocin to cleave ribosomes. E1 RNA contains the conserved cleavage site for restrictocin (SEQ ID NO: 14) 1 μl of E1 RNA was diluted in renaturation buffer (10 mM Tris-HCl, pH 7.6, 50 mM NaCl, 10 mM $MgCl_2$) to a final concentration of 33.3 ng/μl. The solution was incubated at 90° C. for 10 minutes and chilled on ice for 10 minutes to anneal the RNA. The annealed RNA was diluted in reaction buffer (10 mM Tris-HCl, pH 7.6, 50 mM KCL, 4 mM EDTA) and incubated with α-sacrin, restrictocin and restrictocin-I138C-6Histag-hPL conjugate at a final concentration of $1.76\times10^{-6}$ M for 20 minutes at room temperature. Reactions were quenched by 10M urea, 0.05% bromophenol blue solution, and boiling for 2 minutes. The RNA was run on a 20% urea polyacrylamide gel. RNA was visualized by ethidium bromide staining for 10 minutes as shown in FIG. 11. The results show that restrictocin conjugated to hPL was still active, as seen by cleavage of E1 RNA.

The ability of restrictosin to cleave ribosomes was tested. Ribosomes isolated from *E. coli* was diluted in assay buffer (20 mM Tris-HCl, pH 7.6, 2 mM $MgCl_2$, 100 mM $NH_4Cl$) to a final concentration of 1 μM. Restrictocin-I138C-6Histag-hPL was added to a final concentration or $3\times10^{-6}$ M, while the controls received only no enzyme or restrictocin. Samples were incubated for 15 minutes at 37° C. and cooled on ice for 5 minutes and the rRNA was isolated by phenol-chloroform extraction. 2 μg of isolated rRNA was run on a 2% agarose gel. As seen in FIG. 12, restrictocin conjugated to hPL was able to cleave rRNA.

Example 9

Restrictocin-hPL Fusion Protein Preparation

A fusion protein including restrictocin and a prolactin receptor ligand connected by a linker sequence (LS) was prepared. The fusion protein also included a leader sequence and was operably connected to an alkaline phosphatase (phoA) promoter, as shown in FIG. 10. Fusion proteins having different linker lengths were prepared, as shown in Table 1.

TABLE 1

Linker sequences

| Linker Description | Linker length (amino acids) | Amino acid sequence | SEQ. ID |
|---|---|---|---|
| Short linker | 15 | GGGGSGGGGSGGGGS | 2 |
| Long linker | 35 | SSGGGGSTLRDLFDDRAVVLSHYIHNLSSEMFSEGS | 3 |

To introduce restriction sites for XhoI and SalI and remove the stop codon from the end of hPL sequence, Kunkel mutagenesis was performed. Primer for Kunkel mutagenesis (SEQ ID NO:4, shown in Table 2) were phosphorylated in TM buffer (50 mM Tris-HCl, pH 7.5; 10 mM $MgCl_2$). 2 μl of each oligonucleotide (330 ng/μL) was mixed with ATP (1 mM final concentration), DTT (5 mM final concentration), water and T4 polynucleotide kinase (10 U/μl). The reaction mixture was incubated for 30 minutes at 37° C. 2 μl from the reaction was incubated with 1 μg ssDNA (Kunkel template, ssDNA encoding hPL) in TM buffer to anneal the oligonucleotide to the template by treatment at 90° C. for 1 minute, at 50° C. for 3 minutes and incubation at room temperature for 1 hour. The reaction was then ligated overnight at 14° C. with T7 polymerase and transformed into XL1-blue competent cells.

The short linker was added to the Kunkel mutagenized hPL plasmid. The plasmid was digested with XhoI, and dephosphorylated with CIP (Calf Intestinal Phosphatase, NEB, Ipswich, Mass.), and gel purified. Two complementary oligonucleotides with overhangs corresponding to XhoI restriction sites (SEQ ID NO:5 and SEQ ID NO:6, Table 2) where phosphorylated using polynucleotide kinase (NEB, Ipswich, Mass.) for 30 minutes at room temperature, placed at 95° C. and gradually cooled to room temperature to anneal the oligonucleotides. Transformation of 500 ng of the vector with 70 ng of annealed oligonucleotides was performed overnight at 14° C., and transformed into XL1-blue electrocompetent cells.

Restriction sites were added to both ends of the restrictocin sequence using primers shown in Table 2 (SEQ ID NO:11 and SEQ ID NO; 12) by PCR. The restrictocin PCR product was digested with SalI and purified using QIAquick PCR purification Kit. 200 ng of the SalI cut and dephosphorylated plasmid containing the short linker was ligated with 600 ng of the restrictocin after digestion with SalI as described above.

The long linker was added to the Kunkel mutagenized hPL plasmid using the XhoI and SalI restriction sites. The Kunkel mutagenized hPL plasmid was digested with XhoI and SalI for 1 hour, dephosphorylated with CIP for an additional hour, and gel purified. The SalI restriction site was introduced into the restrictocin sequence by PCR as described above. The insert containing the linker and restrictocin sequence was created using PCR overlap extension using the PCR primers (SEQ ID NO:7, SEQ ID NO:8, SEQ ID NO:9 and SEQ ID NO:10) and PCR product of restrictocin with SalI restrictocin sites. The long linker-restrictocin insert was digested for 1 hour at 37° C. using XhoI and SalI and the product was purified using QIAQuick PCR purification Kit (Qiagen, Valencia, Calif.). The digested long linker-restrictocin insert was ligated to the digested and dephosphorylated plasmid using the conditions described above.

TABLE 2

Primer sequences

| Primer Name | Primer Sequence (5'-3') | SEQ ID NO: |
|---|---|---|
| Kunkel mutagenesis | TGGAGGGCAGCTGTGGCTCCTCGAGCTCGTCGAC CTAGGTGCCCGAGTAGCATCC | 4 |
| (G4S)3-sense stand | TCGAGGACGAACCGCCGCCGCCGCTACCACCACC ACCAGAACCGCCACCGCCGC | 5 |
| (G4S)3 antisense strand | TCGAGCGGCGGTGGCGGTTCTGGTGGTGGTGGTA GCGGCGGCGGCGGTTCGTCC | 6 |
| Lo1-primer forward | CCGCTCGAGCGGCGGTGGTGGTTCCACCCTGCGT GACCTGTTCGAC | 7 |
| Lo2-primer forward | GTTCTGTCTCACTACATCCACAACCTGTCCTCTG AAATGTTCTCCGAAGG | 8 |
| Lo1-primer reverse | GTGGATGTAGTGAGACAGAACAACAGCACGGTCG AACAGGTCACGCAG | 9 |
| Lo2-primer reverse | GTTGATGCATGTCCAGGTAGCCGAGGAACCTTCG GAGAACATTTCAGAGGACAGGTT | 10 |
| SalI primer forward | ACGCGTCGACCGCTACCTGGACATGCATC | 11 |
| Sal I primer reverse | TTCCGCGGCCGCTATGGCCGACGTCGACATGAGA ACACAGTCTCAAGTC | 12 |
| Restrictocin forward primer | GCTACCTGGACATGCATCAACCAACAGCTGAATC CCAAGAC | 13 |

Both fusion proteins were expressed in *E. coli* BL21 cells using standard methods, and cell pellets were collected. Cell pellets were lysed for 60 minutes on ice with stirring and then frozen at −70° C. for 1 hour. Cells were defrosted and centrifuged for 25 minutes, 15000 rpm at 4° C. Supernatants were collected, $(NH_4)_2SO_4$ was added to a final concentration of 45%, and proteins were precipitated for 1 hour at 4° C. with stirring. The supernatant was centrifuged at 4° C., 15000 rpm for 35 minutes and pellets were frozen at −20° C. Precipitated protein was analyzed by SDS-PAGE, as shown in FIG. 8.

Example 10

Internalization of hPL-Restrictocin Fusion Proteins

The ability of the fusion protein to cleave ribosomes is measured by incubating with 1 µM ribosomes isolated from *E. coli* in 20 mM Tris-HCl, pH 7.6, 2 mM $MgCl_2$, 100 mM $NH_4Cl$. RNA is purified and visualized by gel electrophoresis as described in Example 8.

A flow cytometric assay is used to determine the ability of the fusion protein to specifically cause apoptosis of cells overexpressing the prolactin receptor. Equal volumes of T47D and SKOV3 cells are mixed, incubated for 24 hours with 0.2 µM or 2 µM fusion protein, a suitable control, or media alone. 24 hours later, cells are stained with anti-prolactin receptor antibodies and a fluorescent secondary antibody. Flow cytometric analysis is conducted to compare cells treated with or without the fusion protein.

Example 11

Delivery of hPL-cMet-siRNA In Vivo

To determine if there is an effect on normal tissue upon delivery of hPL conjugated c-Met-siRNA, the following assay may be used.

Ten nude mice are treated with for 6 weeks with hPL c-Met-siRNA 2 µg/kg administered intraperitoneally. Organ function is monitored by blood serum analysis measuring cbc, electrolyte levels, coagulation factors and LFT. At 6 weeks, mice are sacrificed and organs are excised, fixed in formalin and stained with hemotoxylin and eosin. Organ sections are evaluated for signs of organ damage.

To determine the biodistribution of the hPL-c-Met siRNA conjugate within a subject, the hPL protein is labeled with $^{125}$I using the chloramine T method as described for urokinase in Lengyel et. al., Regulation of urokinase-type plasminogen activator expression by the v-mos oncogene, *Oncogene* 1995; 11:2639-2648, incorporated herein by reference. 2 µg/kg $^{125}$I-hPL/c-Met-siRNA is injected intravenously into female athymic nude mice (Harlan, Indianapolis, Ind.). 24 hours later mice are sacrificed and their tumors and organs are removed and weighed and organ-associated radioactivity is counted. Biodistribution is expressed as a percentage of the injected dose per gram tissue.

Example 12

In Vivo Inhibition of Tumor Growth

The ability of hPL-c-Met siRNA to inhibit invasion and metastasis may be assessed in vivo in an ovarian cancer cell xenograph model as described in Sawada et. al. Cancer Research (2007), 67(4):1670-79. c-Met overexpression is a prognostic factor in ovarian cancer and an effective target for inhibition of peritoneal dissemination and invasion, as described in Sawada et al. *Cancer Research* (2007); 67(4): 1670-1679, incorporated herein by reference in its entirety.

$1 \times 10^6$ CAOV-3 or HeyA8 cells are injected intraperitoneally (ip) on day 0. On day 10, treatment is started by injecting 10 µg/kg hPL/c-Met-siRNA two times a week interperitonally for 4 weeks. Animals are randomly allocated to 5 treatment groups (n=50, 10 per group): Group I: hPL wt c-Met siRNA; Group II: hPL mt c-Met siRNA; Group III: wt c-Met siRNA alone; Group IV: mt c-Met siRNA alone; and Group V: hPL alone with no coupled siRNA. Each group is observed for signs of toxicity including changes in eating and drinking habits, mobility and weight.

At 4 weeks, mice are sacrificed, metastases are counted, ascites and tumor weight are measured. Mouse tumor tissue is excised and a variety of markers known to be involved in ovarian cancer growth and metastasis are performed. Immunohistochemical staining for Ki-67, c-Met, Erk, Stat-1, 5-AKt, Fak and CD31 is performed on tissue sections. Zymography is used to assay for urokinase and MMP-2/9 activity by collecting conditioned media from equal numbers of cells, denaturing and electrophoresing the samples in a 10% SDS-PAGE gel containing 0.2% (w/v) casein with or without 5 µg/ml plasminogen. The gel is incubated at room temperature for 2 hours in the presence of 2.5% Triton X-100 and subsequently overnight at 37° C. in a buffer containing 10 mM $CaCl_2$, 0.15 M NaCl and 100 mM Tris-HCl, pH 7.5. The gel is stained for protein with 0.25% Coomassie blue. Tumor cells are lysed and the lysates are run on a polyacrylamide gel and western blot analysis is performed to assay VEGF concentration within the tumor.

We claim:

1. A method of detecting an ovarian cancer cell comprising a prolactin receptor comprising:

contacting ovarian tissue suspected of comprising a cancer cell with a complex comprising a prolactin receptor ligand selected from human placental lactogen, prolactin, human growth hormone, and human placental lactogen having a I138C substitution, the prolactin receptor ligand coupled to a paramagnetic species for use in magnetic resonance imaging, wherein the prolactin receptor ligand is internalized by cells comprising prolactin receptors;

detecting levels of the paramagnetic species present in the tissue;

and correlating elevated levels of paramagnetic species relative to control tissue with the presence of an ovarian cancer cell in the tissue.

2. The method of claim 1, wherein the paramagnetic species is gadolinium.

3. The method of claim 1, wherein the prolactin receptor ligand is human placental lactogen.

4. The method of claim 1, wherein the prolactin receptor ligand is prolactin.

5. The method of claim 1, wherein the prolactin receptor ligand is human growth hormone.

6. The method of claim 1, wherein the prolactin receptor ligand is human placental lactogen having a I138C substitution.

* * * * *

SEQUENCE LISTING

<160> NUMBER OF SEQ ID NOS: 13

<210> SEQ ID NO 1
<211> LENGTH: 21
<212> TYPE: RNA
<213> ORGANISM: Homo sapiens

<400> SEQUENCE: 1
cugucagagg auacugcacu u                                                 21

<210> SEQ ID NO 2
<211> LENGTH: 15
<212> TYPE: PRT
<213> ORGANISM: Artificial sequence
<220> FEATURE:
<223> OTHER INFORMATION: short linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 36
<212> TYPE: PRT
<213> ORGANISM: Artificial sequence
<220> FEATURE:
<223> OTHER INFORMATION: long linker

<400> SEQUENCE: 3

Ser Ser Gly Gly Gly Gly Ser Thr Leu Arg Asp Leu Phe Asp Asp Arg
1               5                   10                  15

Ala Val Val Leu Ser His Tyr Ile His Asn Leu Ser Ser Glu Met Phe
            20                  25                  30

Ser Glu Gly Ser
        35

<210> SEQ ID NO 4
<211> LENGTH: 55
<212> TYPE: DNA
<213> ORGANISM: Artificial Sequence
<220> FEATURE:
<223> OTHER INFORMATION: Oligonucleotide

<400> SEQUENCE: 4
tggagggcag ctgtggctcc tcgagctcgt cgacctaggt gcccgagtag catcc            55

<210> SEQ ID NO 5
<211> LENGTH: 54
<212> TYPE: DNA
<213> ORGANISM: Artificial Sequence
<220> FEATURE:
<223> OTHER INFORMATION: Oligonucleotide

<400> SEQUENCE: 5
tcgaggacga accgccgccg ccgctaccac caccaccaga accgccaccg ccgc             54

<210> SEQ ID NO 6
<211> LENGTH: 54
<212> TYPE: DNA
<213> ORGANISM: Artificial Sequence
<220> FEATURE:
<223> OTHER INFORMATION: Oligonucleotide

<400> SEQUENCE: 6
tcgagcggcg gtggcggttc tggtggtggt ggtagcggcg gcggcggttc gtcc             54

<210> SEQ ID NO 7
<211> LENGTH: 46
<212> TYPE: DNA
<213> ORGANISM: Artificial Sequence
<220> FEATURE:
<223> OTHER INFORMATION: Oligonucleotide

<400> SEQUENCE: 7
ccgctcgagc ggcggtggtg gttccaccct gcgtgacctg ttcgac        46

<210> SEQ ID NO 8
<211> LENGTH: 50
<212> TYPE: DNA
<213> ORGANISM: Artificial Sequence
<220> FEATURE:
<223> OTHER INFORMATION: Oligonucleotide

<400> SEQUENCE: 8
gttctgtctc actacatcca caacctgtcc tctgaaatgt tctccgaagg        50

<210> SEQ ID NO 9
<211> LENGTH: 48
<212> TYPE: DNA
<213> ORGANISM: Artificial Sequence
<220> FEATURE:
<223> OTHER INFORMATION: Oligonucleotide

<400> SEQUENCE: 9
gtggatgtag tgagacagaa caacagcacg gtcgaacagg tcacgcag        48

<210> SEQ ID NO 10
<211> LENGTH: 57
<212> TYPE: DNA
<213> ORGANISM: Artificial Sequence
<220> FEATURE:
<223> OTHER INFORMATION: Oligonucleotide

<400> SEQUENCE: 10
gttgatgcat gtccaggtag ccgaggaacc ttcggagaac atttcagagg acaggtt        57

<210> SEQ ID NO 11
<211> LENGTH: 29
<212> TYPE: DNA
<213> ORGANISM: Artificial Sequence
<220> FEATURE:
<223> OTHER INFORMATION: Oligonucleotide

<400> SEQUENCE: 11
acgcgtcgac cgctacctgg acatgcatc        29

<210> SEQ ID NO 12
<211> LENGTH: 49
<212> TYPE: DNA
<213> ORGANISM: Artificial Sequence
<220> FEATURE:
<223> OTHER INFORMATION: Oligonucleotide

<400> SEQUENCE: 12
ttccgcggcc gctatggccg acgtcgacat gagaacacag tctcaagtc        49

<210> SEQ ID NO 13
<211> LENGTH: 41
<212> TYPE: DNA
<213> ORGANISM: Artificial Sequence
<220> FEATURE:

```
<223> OTHER INFORMATION: Oligonucleotide

<400> SEQUENCE: 13
gctacctgga catgcatcaa ccaacagctg aatcccaaga c                    41
```